(12) United States Patent
Thevasahayam

(10) Patent No.: US 9,481,622 B2
(45) Date of Patent: Nov. 1, 2016

(54) METHODS AND SYSTEMS FOR PRODUCING ALCOHOLS AND AMIDES FROM CARBON DIOXIDE

(71) Applicant: EMPIRE TECHNOLOGY DEVELOPMENT LLC, Wilmington, DE (US)

(72) Inventor: Arockiadoss Thevasahayam, Tamilnadu (IN)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/660,370

(22) Filed: Mar. 17, 2015

(65) Prior Publication Data
US 2015/0259268 A1 Sep. 17, 2015

(30) Foreign Application Priority Data
Mar. 17, 2014 (IN) .......................... 1401/CHE/2014

(51) Int. Cl.
| | | |
|---|---|---|
| *B01J 19/12* | (2006.01) | |
| *C07C 29/15* | (2006.01) | |
| *B01J 23/745* | (2006.01) | |
| *B01J 35/00* | (2006.01) | |

(Continued)

(52) U.S. Cl.
CPC ................ *C07C 29/15* (2013.01); *B01J 21/04* (2013.01); *B01J 23/745* (2013.01); *B01J 35/002* (2013.01); *B01J 35/0013* (2013.01); *B01J 35/0033* (2013.01); *B01J 37/0072* (2013.01); *B01J 37/0221* (2013.01); *B01J 37/06* (2013.01); *B01J 37/08* (2013.01); *C01G 49/0045* (2013.01); *C07C 231/10* (2013.01); *B01J 23/74* (2013.01); *B01J 37/009* (2013.01); *C01P 2002/72* (2013.01); *C01P 2004/64* (2013.01); *C01P 2006/42* (2013.01)

(58) Field of Classification Search
CPC .... B01J 37/06; B01J 35/0033; B01J 23/745; B01J 37/009; B01J 37/0072; B01J 35/0013; B01J 37/08; B01J 19/12; C07C 29/15; C07C 231/10; C01G 49/0045; C01P 2004/64; C01P 2002/72; C01P 2006/42
USPC ................................ 204/157.81, 157.9, 155
See application file for complete search history.

(56) References Cited

U.S. PATENT DOCUMENTS

| | | | | |
|---|---|---|---|---|
| 2010/0119429 | A1* | 5/2010 | Mullins | ................ C01G 49/08 423/263 |
| 2012/0097521 | A1* | 4/2012 | Shen | ..................... B01J 19/127 204/157.9 |

(Continued)

OTHER PUBLICATIONS

Dejardin et al, "Effect of a dc bias field on the dynamic hysteresis of single-domain ferromagnetic particles," J. Appl. Phys. 107, 073914 (2010).*
Singh et al, "Hysteresis in a magnetic bead and its applications," App. Phys. Lett.. 98, 133702 (2011).*
Singh et al, "Ferromagnetism, hysteresis and enhanced heat dissipation in assemblies of superparamagnetic nanoparticles," J. Appl. Phys. 112, 114912 (2012).*
Salimi et al, "CO2 absorption in manofuluids in a randomly packed column equipped with magnetic field," Heat Mass Transfer (2015) vol. 51, pp. 621-629.*

(Continued)

*Primary Examiner* — Keith Hendricks
*Assistant Examiner* — Colleen M Raphael
(74) *Attorney, Agent, or Firm* — Pepper Hamilton LLP

(57) ABSTRACT

Methods and systems for producing butanol from carbon dioxide, and water are disclosed. In one embodiment, a method of producing butanol from carbon dioxide and water involves contacting carbon dioxide with a reaction mixture containing water and a catalyst, and heating the carbon dioxide and reaction mixture by fluctuating magnetic field. In some embodiments, the catalyst used may be $FeAl_2O_3$.

12 Claims, 4 Drawing Sheets

(51) Int. Cl.
  *C01G 49/00*  (2006.01)
  *B01J 37/00*  (2006.01)
  *B01J 37/08*  (2006.01)
  *B01J 37/06*  (2006.01)
  *C07C 231/10* (2006.01)
  *B01J 21/04*  (2006.01)
  *B01J 37/02*  (2006.01)
  *B01J 23/74*  (2006.01)

(56) References Cited

U.S. PATENT DOCUMENTS

2012/0132538 A1   5/2012   Cole et al.
2012/0288898 A1   11/2012  Lovley et al.

OTHER PUBLICATIONS

Keller et al., Exploiting microbial hyperthermophilicity to produce an industrial chemical, using hydrogen and carbon dioxide Supporting Information, *PNAS* (Apr. 9, 2013), 110(15):5840-5845.

Li et al., Integrated Electromicrobial Conversion of $CO_2$ to Higher Alcohols, *Science* (Mar. 30, 2012), 335(6076):1596.

SN1 and SN2 Reactions, accessed at https://web.archive.org/web/20130722060845/http://iit.edu/arc/workshops/pdfs/SN1_SN2.pdf, accessed on Mar. 9, 2015, pp. 16.

Shen et al., Photosynthetic production of 2-methyl-1-butanol from $CO_2$ in cyanobacterium Synechococcus elongatus PCC7942 and characterization of the native acetohydroxyacid synthase, Energy & Environmental Science (2012), 5:9574-9583.

* cited by examiner

METHODS AND SYSTEMS FOR PRODUCING ALCOHOLS AND AMIDES FROM CARBON DIOXIDE

RELATED APPLICATION

This application claims priority benefit under Title 35 §119(a) of Indian Patent Application No. 1401/CHE/2014, filed Mar. 17, 2014, entitled, "Methods and Systems for Producing Alcohols and Amides from Carbon Dioxide," the contents of which are herein incorporated by reference.

BACKGROUND

Alcohols and amides are important commodity feedstock for a variety of industrial products, and butanol, for example, is used as a precursor for the production of various products, such as adhesives, detergents, dental products, makeup, personal hygiene products, hydraulic brake fluids, paint thinners, pesticides, plastics, synthetic fruit flavorings, vitamins, and the like. Industrially, butanol is produced via gas phase chemistry, using oil and natural gas as feed stocks. 2-butanol is produced via the acid-catalyzed hydration of 1-butene or 2-butene, where 1-butene and 2-butene is obtained via catalytic cracking of petroleum. 1-butanol is produced via the hydroformylation of propylene to butryaldehyde, where the butyraldehyde is subsequently hydrogenated to 1-butanol. In addition to using non-renewable oil and natural gas as feedstocks, the overall process of industrially synthesizing butanol requires a large amount of energy, which generally comes from natural gas. The combustion of natural gas further contributes to increased concentration of carbon dioxide in the atmosphere, and thus contributing to global climate change. Thus, there is a need to develop methods to produce alcohols economically, using easily available resources.

SUMMARY

Disclosed herein are methods to produce butanol from $CO_2$ in the presence of a catalyst $FeAl_2O_3$, by induction heating. In one embodiment, a method of making a catalyst involves contacting a paramagnetic oxide, an amphoteric oxide and a base. In some embodiments, the catalyst may be $FeAl_2O_3$.

In another embodiment, a method of producing butanol from carbon dioxide and water involves contacting carbon dioxide with a reaction mixture comprising water and a catalyst, and exposing the carbon dioxide and reaction mixture to fluctuating magnetic field. In some embodiments, the catalyst used may be $FeAl_2O_3$.

In an additional embodiment, a reactor system for making butanol from carbon dioxide may include a closed reaction vessel configured to receive water, carbon dioxide, and a catalyst, and at least one current carrying element arranged in proximity to a surface of the reaction vessel and configured to heat the reaction vessel by fluctuating magnetic field.

In a further embodiment, a method of producing an amide may include contacting carbon dioxide and nitrogen with a reaction mixture comprising water and a catalyst, and exposing carbon dioxide, nitrogen and the reaction mixture to a fluctuating magnetic field.

In an additional embodiment, a method may include contacting carbon dioxide with water to form a first mixture, contacting the first mixture with a super paramagnetic catalyst to form a second mixture, and exposing the second mixture to a fluctuating magnetic field to form hydroxylated organic materials, wherein the method is carried out at ambient conditions.

In a further embodiment, a method of producing an alcohol may include contacting carbon dioxide with a reaction mixture comprising water and a catalyst, and exposing carbon dioxide and the reaction mixture to a fluctuating magnetic field.

DETAILED DESCRIPTION

Figure 1:
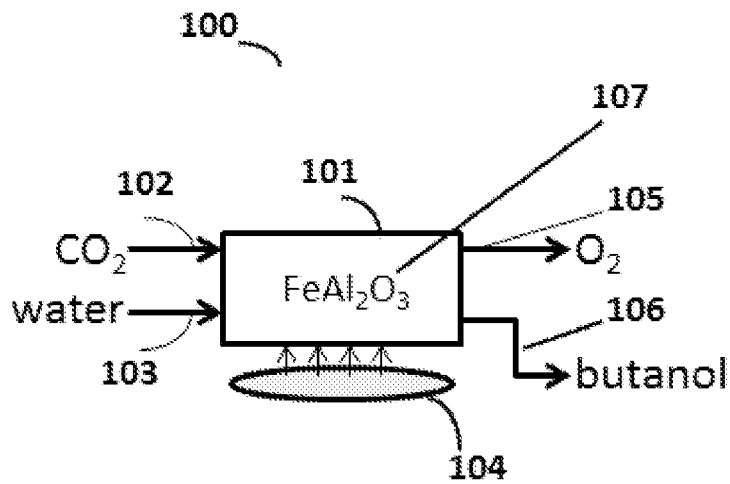
FIG. 1 depicts a diagram of a reactor system to produce butanol from $CO_2$ and water, according to an embodiment.

This disclosure is not limited to particular systems, devices and methods described, as these may vary. The terminology used in the description is for the purpose of describing the particular versions or embodiments only, and is not intended to limit the scope.

The present disclosure is directed to producing butanol from $CO_2$ and water exposing to a fluctuating magnetic field. A catalyst may be employed in this process, such as $FeAl_2O_3$. In some embodiments, a method of making a catalyst may include contacting a paramagnetic oxide, an amphoteric oxide, and a base. Non-limiting examples of paramagnetic oxides that may be used are iron oxide, nickel oxide, cobalt oxide, tin oxide, molybdenum oxide, palladium oxide, rhodium oxide, or any combination thereof. The amphoteric oxides that may be used in this process include, but are not limited to, oxides of Zn, Be, Al, Pb, Si, Ti, V, Fe, Co, Ge, Zr, Ag, Sn, Au, or any combination thereof. In some embodiments, the amphoteric oxide may be ZnO, $Be(OH)_2$, PbO, $Al(OH)_3$, $Al_2O_3$, or any combination thereof. In some embodiments, the base may be $NH_3$, hydrazine hydroxide, or any combination thereof.

In some embodiments, the catalyst $FeAl_2O_3$ may be prepared by contacting $Fe_2O_3$, $Al_2O_3$, and aqueous ammonia. Aqueous ammonia may have a concentration of about 20 weight percent to about 50 weight percent, about 20 weight percent to about 40 weight percent, or about 20 weight percent to about 30 weight percent. Specific examples include about 20 weight percent, about 25 weight percent, about 30 weight percent, about 50 weight percent, and ranges between any two of these values (including their endpoints). In some embodiments, contacting may be accomplished by any suitable means, including mixing, stirring, combining, shaking, agitation, and the like. $Fe_2O_3$, $Al_2O_3$, and aqueous ammonia may be contacted for about 10 minutes to about 1 hour, about 10 minutes to about 45 minutes, about 10 minutes to about 30 minutes, or about 10 minutes to about 20 minutes. Specific examples include about 10 minutes, about 20 minutes, about 30 minutes, about 45 minutes, about 1 hour, and ranges between any two of these values (including their endpoints). In some embodiments, $Fe_2O_3$ and $Al_2O_3$ may be contacted in a molar ratio of about 1:6 to about 1:2, about 1:6 to about 1:3, about 1:6 to about 1:4, or about 1:6 to about 1:5. Specific examples include about 1:6, about 1:5, about 1:4, about 1:3, about 1:2, and ranges between any two of these values (including their endpoints). In some embodiments, $Al_2O_3$, $Fe_2O_3$, and ammonia may be contacted in a molar ratio of about 2:1:2, about 2:1:1, about 1:2:2, about 2:2:1, or about 2:2:2.

After the mixing step, the solvent is evaporated. This step may be performed by any known process in the art, such as heating, rotary evaporation, air drying, Soxhlet extraction, or evaporating in an oven until the solvent is substantially evaporated. For example, the solvent may be heated to about 50° C., about 70° C., about 80° C., or about 100° C., during Soxhlet extraction. In some embodiments, the $FeAl_2O_3$ catalyst obtained may be further subjected to the steps of washing, filtering, and drying. Drying may be generally performed in a furnace by heating to a temperature of about 300° C. to about 800° C., for about 30 minutes to about 6 hours, about 30 minutes to about 5 hours, about 30 minutes to about 3 hours, or about 30 minutes to about 2 hours. Specific examples include about 30 minutes, about 45 minutes, about 2 hours, about 4 hours, about 5 hours, about 6 hours, and ranges between any two of these values (including their endpoints).

In some embodiments, the $FeAl_2O_3$ catalyst is washed with ethanol immediately after the step of drying. This process may impart a paramagnetic property to the catalyst.

Figure 3:
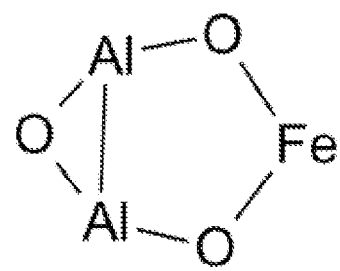
FIG. 3 represents a putative structure of $FeAl_2O_3$ according to an embodiment.

The $FeAl_2O_3$ catalyst obtained by the methods disclosed herein may be a nanoparticle having an average diameter of about 1 nanometer to about 50 nanometers, about 1 nanometer to about 40 nanometers, about 1 nanometer to about 25 nanometers, or about 1 nanometer to about 10 nanometers. Specific examples include about 1 nanometer, about 5 nanometers, about 15 nanometers, about 25 nanometers, about 50 nanometers, and ranges between any two of these values (including their endpoints). A putative structure of $FeAl_2O_3$ catalyst is shown in FIG. 3.

Also disclosed herein are methods to produce butanol from $CO_2$ and water, in the presence of $FeAl_2O_3$ catalyst. Carbon dioxide may be obtained from any source, for example, an exhaust stream from fossil fuel burning power plants, from geothermal or natural gas wells, or the atmosphere itself. Most suitably, the carbon dioxide may be obtained from concentrated point sources of generation prior to being released into the atmosphere. For example, high concentration carbon dioxide sources may frequently accompany natural gas, in flue gases of fossil fuel burning power plants, exhausts from cement factories, from fermenters used for industrial fermentation of ethanol, and from the manufacture of fertilizers and refined oil products.

FIG. 1 depicts an illustrative diagram of a reactor system 100 in accordance with a specific embodiment of the present disclosure. System 100 may be utilized for a one-step process for the production of butanol from carbon dioxide and water. The reactor system (or apparatus) 100 generally comprises a reaction vessel 101, an inlet valve for $CO_2$ 102, an inlet valve for water 103, and a current carrying element 104. A pair of outlet valves for $O_2$ gas 105 and butanol 106 may be present in the reaction vessel 101. The inlet valves may be configured to allow entry of carbon dioxide and water into the reaction vessel. Further, the catalyst $FeAl_2O_3$ 107 may be disposed within the reaction vessel.

In some embodiments, the reactor system 100 comprises at least one current carrying element 104 arranged in proximity to a surface of the reaction vessel and configured to heat the reaction vessel by fluctuating magnetic field. Current carrying elements may be configured to generate magnetic fields of various strengths. The greater the current flow and coil density, the stronger the magnetic field. For instance, coil density may be high in order to produce a uniform magnetic field. In addition, the quantity of power required to achieve a particular magnetic field may depend on various factors, including the scale, structure, and location of the current carrying element with respect to the reaction vessel.

In other embodiments, the reactor system described herein may further comprise a thermoelectric couple, a pressure gauge, a temperature controller, a cooling system, a mechanical stirrer, or any combination thereof.

Figure 2:
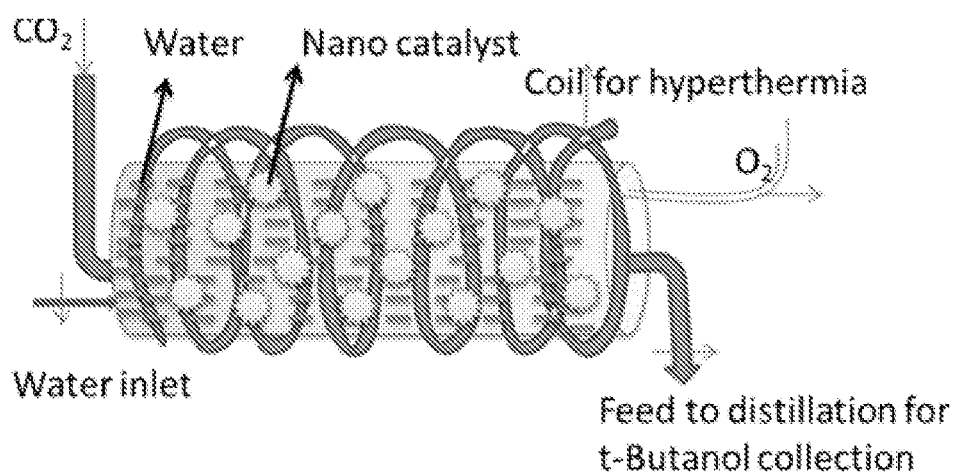
FIG. 2 represents an illustrative diagram of a reactor system to produce butanol from $CO_2$ and water, according to an embodiment.

According to some embodiments, a method of making butanol may include contacting carbon dioxide with a reaction mixture comprising water and a catalyst, and heating the carbon dioxide and reaction mixture by fluctuating magnetic field. In some embodiments, the current carrying element may be in close proximity to the reaction vessel. In other embodiments, the current carrying element may form a circular coil around a reaction vessel, as illustrated in FIG. 2. According to some embodiments, the strength of a magnetic field generated by the current carrying element may be about 0.1 millitesla to about 1 tesla, 0.1 millitesla to about 1 tesla, 0.1 millitesla to about 1 tesla, or a range between any two of these values (including endpoints). The current carrying elements may be energized using various methods, including, without limitation, direct current, alternating current, and high-frequency alternating current. According to embodiments, the high-frequency alternating current may be about 25 hertz (Hz) to about 1 megahertz, about 25 hertz to about 500 kilohertz, or about 25 hertz to about 100 kilohertz. Specific examples include 25 hertz, about 100 hertz, about 500 hertz, about 1 kilohertz, about 300 kilohertz, about 400 kilohertz, about 500 kilohertz, about 1 megahertz, and ranges between any two of these values (including endpoints). In some embodiments, the electric current may be in the range of about 0.1 ampere (A) to about 100 A, about 0.1 ampere to about 50 A, about 0.1 ampere to about 30 A, or about 0.1 ampere to about 1 A. Specific examples include about 0.1 A, about 5 A, about 10 A, about 20 A, about 50 A, about 100 A, and ranges between any two of these values (including endpoints).

The reactor system described herein may be a batch reactor system or a continuous flow reactor system. In some embodiments, the reaction vessel is configured to maintain a constant pressure of carbon dioxide during the reaction process. For example, carbon dioxide may be present at a pressure of about 1 millibar to about 1 bar, about 1 millibar to about 500 millibars, about 1 millibar to about 100 millibars, or about 1 millibar to about 10 millibars. Specific examples include about 1 millibar, about 5 millibars, about 10 millibars, about 15 millibars, about 20 millibars, about 500 millibars, about 1 bar, and ranges between any two of these values (including endpoints).

In some embodiments, the catalyst described herein may be present in the reaction mixture at about 0.1 mole percent to about 1 mole percent, about 0.1 mole percent to about 0.5 mole percent, or about 0.1 mole percent to about 0.2 mole percent of the total reaction mixture. Specific examples include about 0.1 mole percent, about 0.2 mole percent, about 0.5 mole percent, about 0.7 mole percent, about 1 mole percent, and ranges between any two of these values (including endpoints).

In some embodiments, the water may be present in the reaction mixture at about 99 mole percent to about 99.9 mole percent, about 99 mole percent to about 99.6 mole percent, or about 99 mole percent to about 99.3 mole percent of the total reaction mixture.

In some embodiments, the reaction mixture and $CO_2$ are exposed to the fluctuating magnetic field for about 30 minutes to about 3 hours. In some embodiments, the reaction mixture and $CO_2$ are exposed to the fluctuating magnetic field for about 30 minutes to about 2 hours. In some embodiments, the fluctuating magnetic field is applied for about 30 minutes to about 1 hour. In some embodiments, the reaction mixture and $CO_2$ are exposed to the fluctuating magnetic field for about 30 minutes, about 45 minutes, about 1 hour, about 1.5 hours, about 3 hours, or any value or range of values between any of these values (including endpoints).

According to some embodiments, the butanol obtained by the methods described herein may be n-butanol, sec-butanol, isobutanol, ter-butanol, or any combination thereof. Butanol obtained may be isolated by using one or more methods known in the art, including solvent extraction, distillation, and the like. In some embodiments, the paramagnetic catalyst may be recovered at the end of the process by applying a magnetic field. For example, a bar magnet may be used to collect $FeAl_2O_3$ particles at the end of the reaction and reused.

Without wishing to be bound by theory, a possible explanation is provided for the reaction process. When carbon dioxide dissolves in water, it exists in chemical equilibrium producing carbonic acid:

$$CO_2 + H_2O \leftrightarrow H_2CO_3 \leftrightarrow HCO_3^\ominus + H^\oplus$$

At standard temperature and pressure (STP), solubility of the $CO_2$ is 0.65 cm$^3$/g of water. The equilibrium constant at 25° C. in the case of carbonic acid is $[H_2CO_3]/[CO_2] \approx 1.7 \times 10^{-3}$ in pure water and the rate constant is about 0.039 s$^{-1}$.

At room temperature, the reaction between aluminum metal and water to form aluminum hydroxide and hydrogen is as follows:

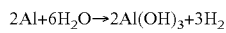

$$2Al + 6H_2O \rightarrow 2Al(OH)_3 + 3H_2$$

Figure 4:
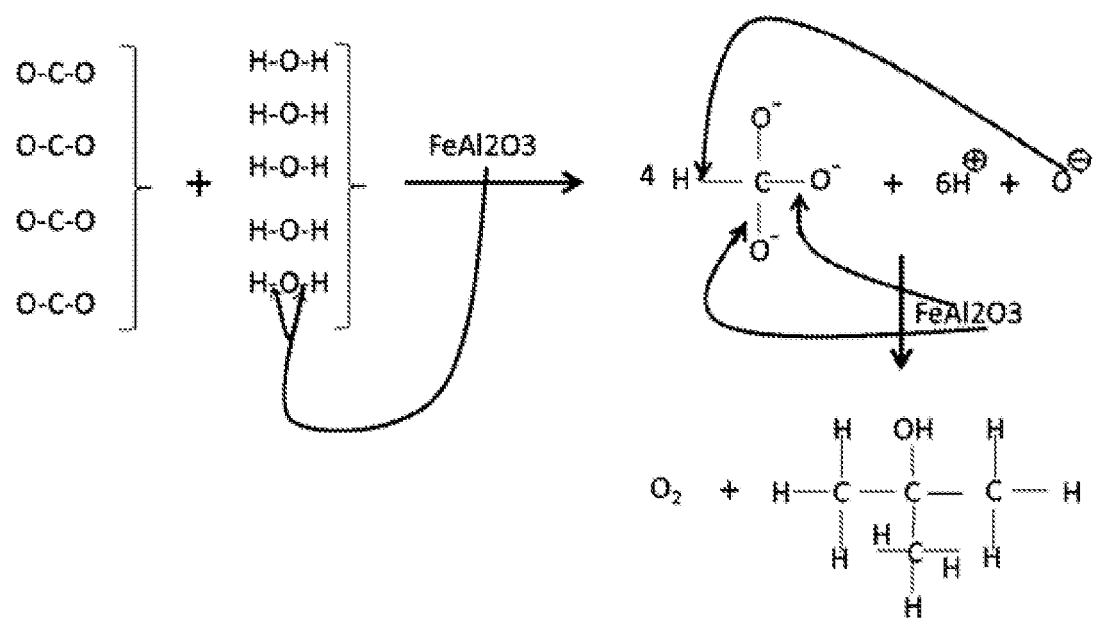
FIG. 4 represents schematics of SN1 mechanism involved in production of butanol from $CO_2$ and water, according to an embodiment.

Further, Al forms a loose bond with O in $H_2O$ and dissolved $CO_2$, characteristic of weak van der Waals forces. In the presence of a fluctuating electromagnetic field, the catalyst gets heated up (paramagnetic related hysteresis), resulting in breaking up of O—H and O—C bonds, thereby releasing gases $O_2$ from $HCO_3^-$, $H_2$ and $O_2$ from $H_2O$. This can be represented by a SN1 mechanism, as shown in FIG. 4. SN1 is a two-step reaction involving the initial formation of a planar carbocation formation by the loss of the leaving group ($H^+$). The carbocation that is formed is attacked by the nucleophile $O^-$. Since the carbocation is not particularly stable, neighboring carbocations that are present donate electron density into the carbocation to help stabilize it, thus forming ter-butanol. The above SN1 mechanism may explain the formation of ter-butanol.

EXAMPLES

Example 1

Preparation of Catalyst $FeAl_2O_3$

Figure 5:
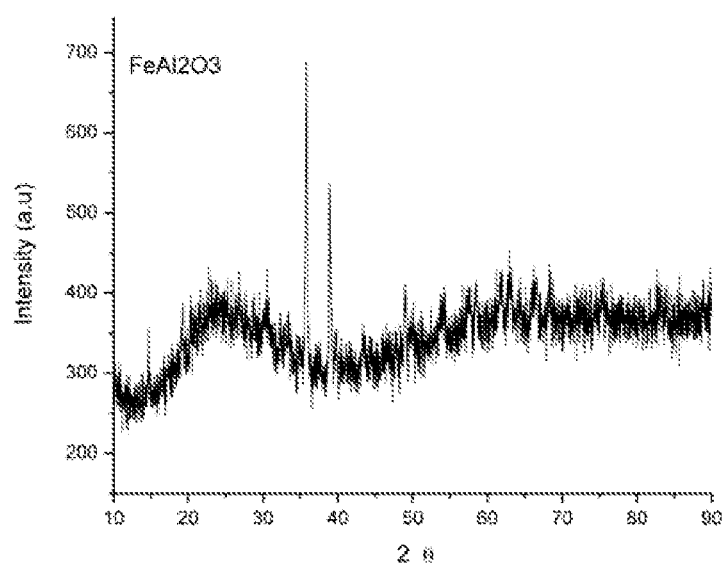
FIG. 5 depicts X-ray diffraction pattern of $FeAl_2O_3$ according to an embodiment. The XRD was acquired on a Xperts Pananalytical X-Ray diffractometer using Ni-filtered CuKα radiation ($\lambda$=0.15418 nm) with a scanning range (2θ) of 10 to 90. The peak 2θ at 35.89 correspond to Aluminum oxide of pcpdf file 89-7408 and Miller indices (hk1) value (110).
Figure 6:
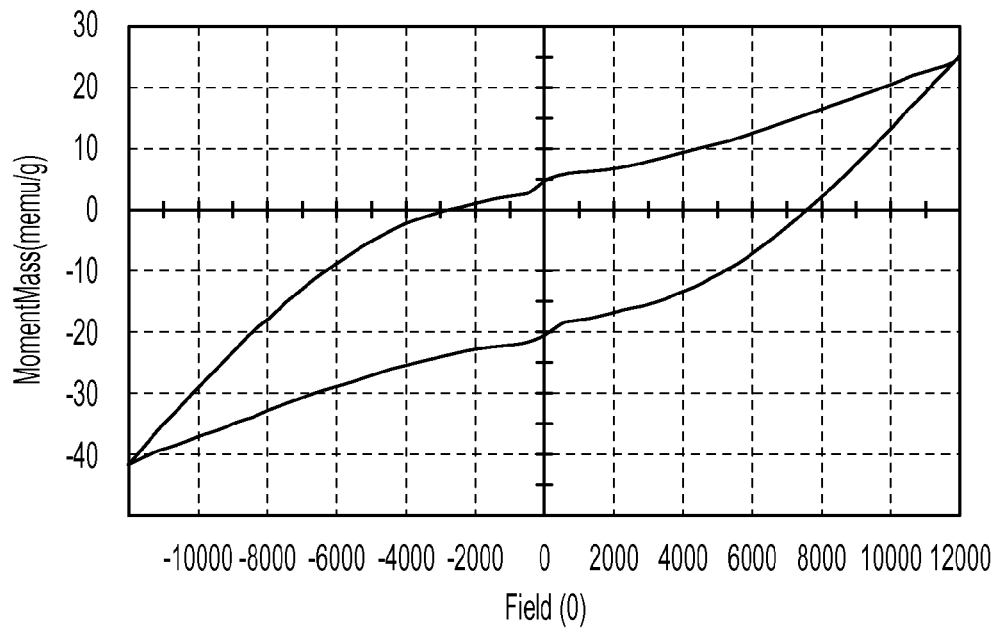
FIG. 6 shows vibrating sample magnetometer measurements of $FeAl_2O_3$ catalyst according to an embodiment.

About 3 grams of $Fe_2O_3$ and 6 grams of $Al_2O_3$ were dispersed in 50% ammonia solution, and stirred continuously for 15 to 30 minutes. The solution was transferred to a Soxhlet apparatus and maintained at 100° C. until all the excess solvent was evaporated. The residue was washed with distilled water until a pH of 7 was reached. After filtering, the residue powder was dried in a furnace for 1 hour at 700° C., removed and about 10 mL of ethanol was added immediately. The catalyst thus prepared was characterized by X-ray diffraction (FIG. 5) and used for experiments described below.

Example 2

Production of Butanol from $CO_2$ and Water

About 500 milligrams of $FeAl_2O_3$ catalyst prepared in Example 1 was dispersed in 20 mL of water in three neck flask, connected to $CO_2$ cylinder and a gas collection chamber. The flask was purged with $CO_2$ gas for 2-3 minutes, and the outlet valve was closed, thereby allowing the pressure to build-up in flask. The $CO_2$ pressure was maintained at 20 millibar during the entire reaction process. The flask was heated by fluctuating magnetic field by supplying an electric current of 230V, 50 Hz, 240 mA for 60 minutes (magnetic field about 1000 μtesla). During the reaction process, the outlet valve was opened to collect various gases that were released. The product ter-butanol obtained was confirmed by NMR. The $FeAl_2O_3$ catalyst was recovered using simple magnets (0.03 T) for reuse.

Example 3

Production of Butanol from $CO_2$ and Water

The apparatus was set up as in Example 2 and various parameters were changed to analyze the effect on butanol yield. Table 1 shows the yield of butanol obtained in response to various amounts of catalyst used. The volume of water (20 mL) and the $CO_2$ pressure (20 millibar) were kept constant in all the experiments.

TABLE 1

| S. No | Time of exposure (min.) | Catalyst (mg.) | Volume of water (mL) | Butanol after distillation (mL) | Water remaining | Butanol yield (%) |
|---|---|---|---|---|---|---|
| 1 | 30 | 100 | 20 | 7.5 ± 0.4 | 12.5 ± 0.3 | 37.5 |
| 2 | 30 | 200 | 20 | 10.8 ± 0.3 | 9.2 ± 0.3 | 54 |
| 3 | 30 | 300 | 20 | 12.9 ± 0.2 | 5.1 ± 0.2 | 64.5 |
| 4 | 30 | 400 | 20 | 14.2 ± 0.2 | 2.8 ± 0.2 | 71 |
| 5 | 30 | 500 | 20 | 16.5 ± 0.1 | 0.5 ± 0.1 | 82.5 |

The process was repeated and the time of exposure to electromagnetic field was varied. The volume of water (20 mL), catalyst (500 milligrams), and the $CO_2$ pressure (20 millibar) were kept constant throughout the process. The percent yield of butanol are shown in Table 2.

TABLE 2

| S. No | Time of exposure (min.) | Catalyst (mg.) | Volume of water (mL) | Butanol after distillation (mL) | Water remaining | Butanol yield (%) |
|---|---|---|---|---|---|---|
| 1 | 30 | 500 | 20 | 16.4 ± 0.2 | 3.5 ± 0.4 | 82 |
| 2 | 60 | 500 | 20 | 17.1 ± 0.2 | 3 ± 0.3 | 85.5 |
| 3 | 90 | 500 | 20 | 18.3 ± 0.2 | 1.6 ± 0.5 | 91.5 |
| 4 | 120 | 500 | 20 | 19.5 ± 0.2 | 0.5 ± 0.1 | 97.5 |

Further, the amount of $CO_2$ was varied and the percent yield of butanol was calculated, as shown in Table 3. Exposure time was 120 minutes in all studies.

TABLE 3

| S. No | Chamber pressure (mbar) | Catalyst (mg.) | Volume of water (mL) | Butanol after distillation (mL) | Water remaining | Butanol yield (%) |
|---|---|---|---|---|---|---|
| 1 | 1  | 500 | 20 | 5.3 ± 0.2  | 14.7 | 26.5 |
| 2 | 5  | 500 | 20 | 8.2 ± 0.2  | 11.8 | 41   |
| 3 | 10 | 500 | 20 | 11.5 ± 0.2 | 8.5  | 57.5 |
| 4 | 15 | 500 | 20 | 14.7 ± 0.2 | 5.3  | 73.5 |
| 5 | 20 | 500 | 20 | 19.5 ± 0.2 | 0.5  | 97.5 |

These studies demonstrated that higher catalyst loading, increased exposure time to fluctuating magnetic field, and higher $CO_2$ pressure increased butanol yields.

Example 4

Production of Butanol from Flue Gas

About 10 grams of $FeAl_2O_3$ catalyst prepared in Example 1 is dispersed in 100 L of water in a reaction vessel, and connected to a flue gas source which comprises 50% $CO_2$. The vessel is purged with flue gas for 5-10 minutes, and the outlet valve was closed, thereby allowing the pressure to build-up in vessel. The gas pressure is maintained at 50 millibar during the entire reaction process. The vessel is heated by fluctuating magnetic field by supplying an electric current of 230V, 500 Hz, 240 mA for 60 minutes (magnetic field about 100 millitesla). During the reaction process, the outlet valve is opened to collect various gases that are released. The product ter-butanol obtained is confirmed by NMR.

Example 5

Production of Butanol from Natural Gas

About 10 grams of $FeAl_2O_3$ catalyst prepared in Example 1 is dispersed in 100 L of water in a reaction vessel, and connected to a natural gas source which comprises 30% $CO_2$. The vessel is purged with natural gas for 5-10 minutes, and the outlet valve was closed, thereby allowing the pressure to build-up in vessel. The gas pressure is maintained at 50 millibar during the entire reaction process. The vessel is heated by fluctuating magnetic field by supplying an electric current of 230V, 500 Hz, 240 mA for 60 minutes (magnetic field about 100 millitesla). During the reaction process, the outlet valve is opened to collect various gases that are released. The product ter-butanol obtained is confirmed by NMR.

Example 6

Production of Amides from $CO_2$, $N_2$, and Water

About 500 milligrams of $FeAl_2O_3$ catalyst prepared in Example 1 is dispersed in 20 mL of water in three neck flask, connected to $CO_2$ cylinder, $N_2$ cylinder, and a gas collection chamber. The flask is purged with $CO_2$ and $N_2$ gases for 2-3 minutes, and the outlet valve is closed, thereby allowing the pressure to build-up in flask. The partial pressures of $CO_2$ and $N_2$ are maintained at about 20-40 millibars during the entire reaction process. The flask is exposed to fluctuating magnetic field by supplying an electric current of 230V, 50 Hz, 240 mA for 60 minutes (magnetic field about 1000 µtesla). During the reaction process, the outlet valve is opened to collect various gases that will be released. The product including amides is formed and can be confirmed by NMR. The $FeAl_2O_3$ catalyst is recovered using simple magnets (0.03 T) for reuse.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of producing butanol from carbon dioxide and water, the method comprising: contacting carbon dioxide with a reaction mixture comprising water and a superparamagnetic catalyst; and exposing carbon dioxide and the reaction mixture to a fluctuating magnetic field at ambient conditions to produce butanol.

2. The method of claim 1, wherein the method further comprises maintaining a constant pressure of carbon dioxide of about 1 millibar to about 1 bar during the exposing step.

3. The method of claim 1, wherein contacting comprises contacting carbon dioxide with the reaction mixture comprising water and the superparamagnetic catalyst, wherein the superparamagnetic catalyst is present at about 0.1 mole percent to about 1 mole percent of the total reaction mixture.

4. The method of claim 1, wherein exposing comprises exposing carbon dioxide and the reaction mixture to the fluctuating electromagnetic field generated by an electrical current having a range of about 0.1 ampere (A) to about 100 A, and at a frequency in a range of about 25 hertz (Hz) to about 1 megahertz.

5. The method of claim 1, wherein exposing comprises exposing carbon dioxide and the reaction mixture to the fluctuating electromagnetic field that is in the range of about 0.1 millitesla to about 1 tesla for about 30 minutes to about 3 hours.

6. The method of claim 1, wherein producing butanol comprises producing n-butanol, sec-butanol, isobutanol, ter-butanol, or any combination thereof.

7. The method of claim 1, further comprising recovering the superparamagnetic catalyst after the production of butanol.

8. The method of claim 1, wherein contacting comprises contacting carbon dioxide with the reaction mixture comprising water and a superparamagnetic catalyst comprising $FeAl_2O_3$ nanoparticles.

9. A method comprising: contacting carbon dioxide with water to form a first mixture; contacting the first mixture with a superparamagnetic catalyst to form a second mixture; and exposing the second mixture to a fluctuating magnetic field to form alcohol, wherein the method is carried out at ambient conditions.

10. The method of claim 9, wherein contacting the first mixture comprises contacting the first mixture and $FeAl_2O_3$ to form the second mixture, wherein $FeAl_2O_3$ is present at about 0.1 mole percent to about 1 mole percent of the second mixture.

11. The method of claim 9, wherein exposing the second mixture comprises exposing the second mixture to the fluctuating magnetic field to form butanol.

12. The method of claim 9, wherein the superparamagnetic catalyst comprises $FeAl_2O_3$ nanoparticles.

* * * * *